United States Patent [19]

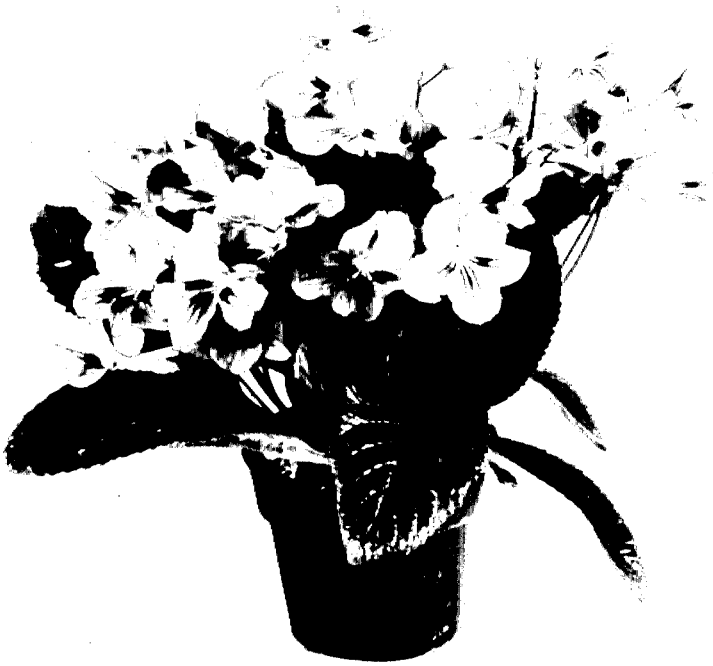

Hopka

[11] Patent Number: Plant 5,562

[45] Date of Patent: Sep. 24, 1985

[54] DISTINCT VARIETY OF STREPTOCARPUS NAMED TEAL

[76] Inventor: Christian Hopka, 106 E. Lakeview St., Madison, Wis. 53716

[21] Appl. No.: 560,152

[22] Filed: Dec. 12, 1983

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new cultivar of *Streptocarpus X hybridus* plant is characterized by abundant violet flowers and a compact vigorous plant habit.

1 Drawing Figure

BACKGROUND OF THE NEW PLANT

The present invention comprises a new and distinct cultivar of Cape Primrose (*Streptocarpus x hybridus* Voss.) known by the name of Teal. This selection was developed for the commercial greenhouse industry as a flowering potted plant. Teal exhibits compact, vigorous growth, improved heat tolerance, and abundant flower production under progressive commercial practices. The flower color, shape and pattern offers a novel combination not previously available.

In 1978 an ideotype breeding program was initiated to improve the characteristics of Cape Primroses for commercial production. Weismoor Hybrids, J. Innes, Hybrids, "Constant Nymph" Series, Oglevee's Bavarian Bells, and cultivars of unknown origin were intermated using conventional breeding procedures. $F_1$ selections were selfed and the best progenies used as background parents for the ideotype. Breeding lines were established in each of the major color classes in the $F_3$ generation. Selection criteria included floriferousness, good foliage quality and symmetrical compact habit. The pedigree of Teal is as follows:

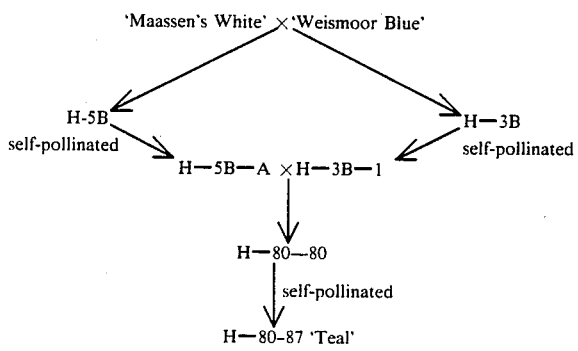

The new cultivar was first asexually reproduced by leaf cuttings in the University of Wisconsin Department of Horticulture greenhouses in Madison, Wis., in 1979. It has been found to retain its distinctive characteristics through successive propagations.

This new cultivar was evaluated by a jury of industry specialists and professional plant breeders for aesthetic qualities, and screened though production trials for desireable propagation, production and flowering characteristics.

The new cultivar, when grown in a greenhouse in Madison, Wis. has a response time of about 10½ weeks. This response time is measured from the potting of plantlets in a five inch pot to the time when the plant has six flowers. Anthesis was about 8½ weeks after potting.

DESCRIPTION OF THE DRAWING

The accompanying photograph illustrates the new cultivar, the color being as nearly true as possible with color illustrations of this type.

DESCRIPTION OF THE NEW PLANT

The botanical description of the new cultivar follows. The data was collected from asexually propagated plants produced at the University of Wisconsin-Madison, Department of Horticulture. The plant histories were taken on 14-week old plants produced in a double-layered polyethylene greenhouse under natural light. Color readings were taken indoors under cool-white fluorescent light. Color references are those displayed in The Royal Horticultural Society Colour Chart.

Botanical classification: Gesneriaceae (Family); *Streptocarpus x hybridus* (Genus x species).

Flower:

*Size and shape.*—Fully expanded 65–70 mm, Corolla gamapetalous, 5-lobed, and distinctly bilabiate.

*Borne.*—Flowers are borne in a branched cymose dichasium singly or in clusters up to four flowers.

*Color.*—Front of petals. Upper 2 petals Methyl Violet (39/1), lower 3 petals Methyl Violet overlaid with a dark Aster Violet (38) veining pattern that diffuses out from the darker throat area. Yellow throat markings (601/1) extend out as 2 distinct lines along adnation of lower 3 petals. Reverse of petals. (37/2)

*Reproductive structures.*—Ovaries — 25–28 mm long and 1½ mm wide. Stamens — arising from base of petals and adnate for 25–28 mm — free for 7 mm. The anterior 2 fertile, 2 lateral staminodes present. Stems — Approx. 16 cm long.

Foliage:

*Size and shape.*—Leaves oblanceolate to obovate with ruffled margins and crenate margins. Approx. 6–8 cm wide and 20–24 cm long.

*Color.*—Top side of leaves 0960 Spinach Green, and underside 0960/3.

Plant:

*Habit.*—Leaves form a rosette from a crown at the soil line. Height from soil line 23 cm. Spread of mature plant 35 cm.

I claim:

1. A new and distinct variety of Streptocarpus substantially as herein shown and described.

* * * * *